United States Patent [19]

Katsuen et al.

[11] Patent Number: 5,643,561

[45] Date of Patent: Jul. 1, 1997

[54] COATING COMPOSITION FOR CULTURING ANIMAL CELLS AND METHOD FOR CULTURING OF THE CELLS IN SERUM-FREE CONDITION

[75] Inventors: Susumu Katsuen; Kunihiro Ohshima, both of Osaka; Seiko Kawamura, Shijonawate; Ryohei Yamamoto, Takatsuki; Toyokazu Nishino, Ibaraki, all of Japan

[73] Assignee: Kurashiki Boseki Kabushiki Kaisha, Kurashiki, Japan

[21] Appl. No.: 334,017

[22] Filed: Nov. 2, 1994

Related U.S. Application Data

[63] Continuation of Ser. No. 49,404, Apr. 20, 1993, abandoned.

[30] Foreign Application Priority Data

Apr. 21, 1992 [JP] Japan .................. 4-100932
Sep. 3, 1992 [JP] Japan .................. 4-235806

[51] Int. Cl.⁶ .................................................. A61K 31/74
[52] U.S. Cl. .................. 424/78.17; 424/78.18; 424/78.22; 424/487; 435/70.3; 435/402; 435/399; 435/396; 435/395
[58] Field of Search .................. 424/548, 572, 424/484, 582, 78.18, 78.22, 407, 418, 77, 78.17; 530/350; 435/70.3, 240.2, 177–180; 514/21

[56] References Cited

U.S. PATENT DOCUMENTS

| | | | |
|---|---|---|---|
| 4,970,298 | 11/1990 | Silver et al. | 530/356 |
| 5,183,804 | 2/1993 | Saiki et al. | 514/12 |
| 5,196,190 | 3/1993 | Nangia et al. | 424/78.06 |
| 5,219,895 | 6/1993 | Kelman et al. | 522/68 |

FOREIGN PATENT DOCUMENTS 0382214 8/1990 European Pat. Off. .

OTHER PUBLICATIONS

Jun. 1990 EP-A-0 373 626 (Mitsubishi Kasei Corporation).
Nov. 1990 WO-A-90 14417 (Synbiotics Corporation).
Apr. 1991 WO-A-91 05036 (Board of Regents, The University of Texas).

*Primary Examiner*—Neil S. Levy
*Attorney, Agent, or Firm*—Foley & Lardner

[57] ABSTRACT

Disclosed is a coating compositions for culturing animal adhesive cells comprising a water-insoluble polymer dissolved in a lower alcohol or an aqueous lower alcohol which enable to enhance the adhesive ability and growth of the adhesive cells. Also disclosed is serum-free cell culturing method using culture vessels or carrier coated with the water-insoluble polymer having cell adhesive activity on at least a part of the surface which enable to not only culture but also subculture a variety of adhesive cells including vascular endothelial cell under serum-free condition.

20 Claims, 2 Drawing Sheets

COATING COMPOSITION FOR CULTURING ANIMAL CELLS AND METHOD FOR CULTURING OF THE CELLS IN SERUM-FREE CONDITION

This application is a continuation, of application Ser. No. 08/049,404, filed Apr. 20, 1993 abandoned.

BACKGROUND OF THE INVENTION

1. Field of the Invention

The present invention relates to a coating composition for culturing cells, which enhances the adhesive property and growth of adhesive cells. The present invention also relates to a serum-free culturing method of animal adhesive cells.

2. Prior Art

In the field of biotechnology, techniques of cell culture have been developed extensively for the production of such substances that are difficult to obtain by synthesis as antibodies, hormones, enzymes, nucleic acids and other physiologically active compounds by utilizing animal cells. These animal cells are divided into suspended cells and adhesive cells, and the former are relatively easy to culture since they can proliferate in suspension of the medium. By contrast, the latter requires to adhere on the inner surface of culture vessel and can grow only on the solid surface. Therefore, the state and characteristics of the inner surface of the vessel or carrier onto which the cells adhere influence greatly on the cell growth and functions of the cells.

Previously, glass or plastic vessel for cell culture have been used, but their intact surface lacks sufficient hydrophilicity so that cell attachment onto the surface and cell growth has not been satisfactory.

For overcoming the difficulty, a method of making the inner surface of a cell culture vessel hydrophilic by special plasma treatment (see Japanese Patent Laid-Open Publication No. 76570/1990), and another one in which the inner surface is coated with cell adhesive proteins such as collagen, gelatin and fibronectin (see Japanese Patent Laid-Open Publication No. 71884/1983), have been commonly practiced.

However, the plasma treatment requires expensive plasma generating and gas exchanging apparatus and a long time with the result of high operation cost. In addition, since the treatment is done by batches, there may occur difference in some lots. The plasma-treated vessels don't have sufficient thermostability for heating treatment such as sterilization in autoclave. With some kind of cells, their adhesive and proliferative properties are rather deteriorated (see Japanese Patent Laid-Open Publication No. 109769/1988).

Further, purification of adhesive proteins such as collagen and gelatin to a high quality grade for use in cell culture requires complicated procedures, special apparatus and expensive reagents with the result of raising the cost of the final product. In addition, the coated vessels are short in thermostability for sterilization in autoclave or other heating treatments, and sterilization by γ-rays causes partial degradation of the proteins to deteriorate the cell adhesion (see Japanese Patent Laid-Open Publication No. 234670/1990).

In addition, purification of collagen to a degree for use in cell culture requires considerable steps of processing and still a satisfactory purity cannot be achieved usually. Impurities in collagen, often are causes of contamination in the physiologically active substances produced by the cells. Further, many enzymes produced by cells by themselves not only make a cause of contamination but also work in long culture to decompose collagen causing release of the adhered cells from inner surface of the culture vessel. Further more, there are such problems as considerable difference in impurities among lots, and low thermostability of collagen makes impossible to sterilize the coated vessels in autoclave (see Japanese Patent Laid-Open Publication No. 291260/1990).

On the other hand, conventional methods for coating the inner surface of cell culture vessel with a synthetic polymer are, for example, the method in which a synthetic polymer is molded into a film which can be used as it is for cell culture, and that a synthetic polymer is suspended or dissolved in benzene, dioxane, N,N'-dimethylformamide or other organic solvent, the suspension or solution is applied over the inner surface of cell culture vessel, then the solvent is removed and the vessel is sterilized by autoclaving or γ-rays irradiation (see Japanese Patent Laid-Open Publication No. 89179/1983). However, in the former method, a new apparatus is required and handling is time-consuming, while in the latter method, required to allow the vessel to stand for a definite time for coating of the polymer over the surface, and then the solvent is required to be removed by suction or drying with heating before the vessel is sterilized. When a water-soluble polymer is used as a coating polymer, there may occur that releasing and dissolving of the polymer into the medium during the cell culture. When a synthetic polymer dissolved in such an organic solvent as benzene, dioxane and N,N'-dimethylformamide is used for coating over the surface of culture vessel or other materials, ordinary commercially available culture vessels made of polystyrene or other plastic materials may be dissolved by the organic solvent and so the culture vessels to be used are limited to those made of organic solvent-resistant materials.

It is also noted that due to the fact that animal adhesive cells grow only when they adhere onto inner surface of culture vessel, culture of the cells is usually done by employing a serum-containing medium. Serum is comprising a variety of components including vitronectin that works to make the cells to be able to adhere onto the surface of the culture vessel.

It must be pointed out, however, serum is very expensive composition, the components are varying in lots and volume of one lot is limited. Therefore, problems are also present that complicated procedures are required at every change of the lot for check of quality and regulation and management of the culture conditions according to the quality. In addition, since serum is a mixture containing numerous substances with physiological activities which are released from blood cells and vascular endothelial cells, analysis or utilization of the products of cultured cells in a serum-containing medium requires procedures for high purification.

To solve the above discussed problems establishment of a serum-free culturing method of animal adhesive cells is desired.

Previously a number of serum-free culturing method of animal adhesive cells have been proposed. Reported examples are a method of culturing vascular endothelial cells in a serum-free medium to which heparin and a cell growth factor are added (see Japanese Patent Laid-Open Publication No. 187083/1989), a method of culturing vascular endothelial cells in a serum-free medium to which zinc or copper salt is added (see Japanese Patent Laid-Open Publication No. 97379/1990) and a method of a serum-free culturing method of fibroblasts by using a specific polystyrene-type polymer as a substrate (see Japanese Patent Laid-Open Publication No. 279787/1988). However, each of these methods has a limitation in cell species and so lacks universal applicability.

SUMMARY OF THE INVENTION

The present invention has been carried out in order to provide a coating composition for culturing adhesive cells whereby the above discussed problems concerning the adhesion and growth of the cells are dissolved, and the adhesive property and growth of the cells are enhanced in a simple and effective manner without requirement of a special apparatus and additional sterilizing treatment. Further, the present invention has also been carried out in order to provide a serum-free culturing method for the variety of adhesive cells including vascular endothelial cells.

According to one aspect of the present invention there is provided a coating composition for culturing adhesive cells comprising a water-insoluble polymer dissolved in a lower alcohol or an aqueous lower alcohol. Coated layer of the coating composition formed on a surface of a culture vessel acts as a matrix in culturing animal adhesive cells.

According to the another aspect of the present invention, there is provided a serum-free culturing method of animal adhesive cells using a culture vessel or a carrier coated with the water-insoluble polymer having cell adhesive activity on at least a part of the surface and culturing the animal adhesive cells in contact with the polymer.

BRIEF DESCRIPTION OF THE DRAWINGS

These and other objects and features of the present invention will become clear from the following description taken in conjunction with the preferred embodiments thereof with reference to the accompanying drawings.

DETAILED DESCRIPTION OF THE INVENTION

Figure 1:
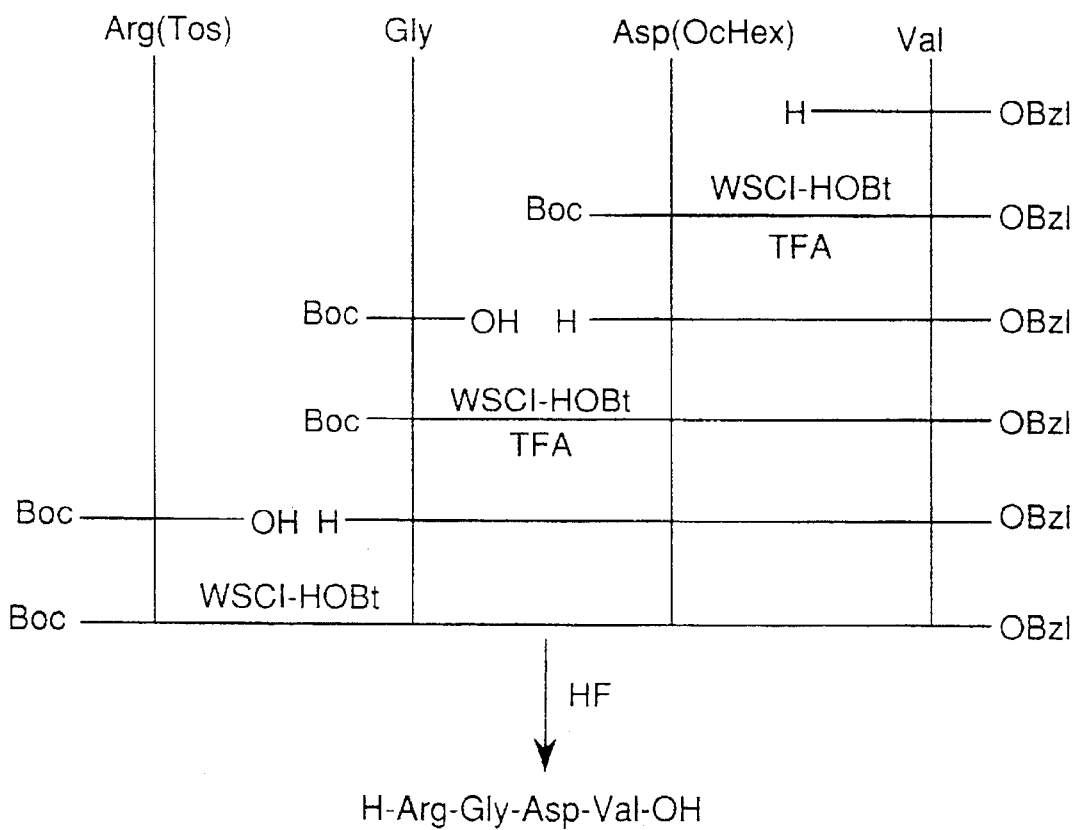
FIG. 1 shows a scheme for synthesis of cell adhesive peptide RGDV.

The coating composition for culturing adhesive cells in the present invention is prepared by dissolving a water-insoluble polymer to an adequate concentration in a lower alcohol or an aqueous lower alcohol. The preferable solvent is the alcohols containing 1–4 carbon atoms, for example methanol, ethanol, propanol and butanol or a mixed solvent made of the lower alcohol and water, for example 50–90% aqueous methanol, ethanol and propanol. According to the present invention, concentration of the water-insoluble polymer in the coating composition may be in a range between 0.0001% (1 μg/ml) and 0.1% (1 mg/ml), and preferably between 0.0001 and 0.01%.

In the present invention, a variety of water-insoluble polymers that are soluble in a lower alcohol or an aqueous lower alcohol may be employed, preferable polymer that is used generally in the invention is a copolymer of monomers selected from the group consisting of hydrophobic monomer, positively charged monomer, negatively charged phosphate-type monomer, monomer chemically modified with a protein or a peptide and the mixture thereof and a hydrophilic monomer.

Examples of the hydrophilic monomers that may be used in the present invention are hydroxyethyl (metha)acrylate [in this Specification "(metha)acrylate" signifies acrylate and methacrylate], hydroxypropyl (metha)acrylate, glycerol (metha)acrylate, pentaerythritol (metha)acrylate, oligoethyleneglycol (metha)acrylate and oligopropyleneglycol (metha)acrylate.

Examples of the hydrophobic monomers that may be used in the present invention are methyl (metha)acrylate, ethyl (metha)acrylate, n-propyl (metha)acrylate, isopropyl (metha)acrylate, n-butyl (metha)acrylate, isobutyl (metha)acrylate and t-butyl (metha)acrylate.

Examples of the positively charged monomers that may be used in the present invention are dimethylaminomethyl (metha)acrylate, diethylaminoethyl (metha)acrylate and dimethylaminoethyl (metha)acrylate.

Examples of the negatively charged phosphate-type monomers that may be used in the present invention are represented by the following general formula (I):

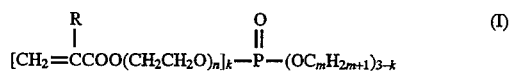

(wherein R represents hydrogen or methyl group, k is a number of 1 or 2, n is a number of 0–30 and m is a number of 0–8).

According to the present invention, the monomer chemically modified with a protein or a peptide may be a (metha) acrylic acid derivative chemically modified with a protein or a peptide. Examples of the protein are gelatin such as protease-treated gelatin and keratin such as the keratin obtained by oxidative degradation of animal hair, and examples of the peptide are those having a cell adhesive activity so called cell adhesive peptide.

Many of cell adhesive peptides have now been known from the analysis of the active site of proteins having cell adhesive activity such as fibronectin or laminin. The peptide to be employed in the invention may be any that has a cell adhesive activity, and any known one may be selected according to the kind of cell to be cultured. Since the cell adhesive potency of the peptides show some selectivity, selection of the cell adhesive peptide adequate for the cells to be cultured will enable purification of the cells. For example, in the culture of vascular endothelial cells, vascular smooth muscle cells that are present as contaminant can be removed from the culture.

Examples of cell adhesive peptide that used in the present invention are RGDV (Arg-Gly-Asp-Val), RGDS (Arg-Gly-Asp-Ser), RGDN (Arg-Gly-Asp-Asn), DGEA (Asp-Gly-Glu-Ala) and YIGSR (Tyr-Ile-Gly-Ser-Arg). These peptides may be synthesized from respective amino acids by conventional methods.

In this specification amino acids, peptides and protective groups are shown by the following abbreviations:

| | | | |
|---|---|---|---|
| Ala: | L-alanine | Glu: | L-glutamic acid |
| Arg: | L-arginine | Gly: | L-glycine |
| Asn: | L-asparagine | Ser: | L-serine |
| Asp: | L-aspartic acid | Tyr: | L-tyrosine |
| Ile: | L-isoleucine | Val: | L-valine |
| Boc: | t-butyloxycarbonyl | OBzl: | benzyl |
| OcHex: | cyclohexyl | Tos: | tosyl |

Examples of the monomer that may be used for the reaction with the above cell adhesive peptide are (metha)acrylic acid, (metha)acrylamide, glycidyl (metha)acrylate and N-(metha)acryloyloxysuccinimide.

It is desirable to introduce a cell adhesive peptide into the water-insoluble polymer in a rate higher than 2 μg/mg. When the amount of the cell adhesive peptide is less than 2 μg/mg, coating of the inner surface of a culture vessel with such polymer will not increase sufficiently the adhesion of the cultured cells so that effective growth of the cells cannot be expected.

In preparing the water-insoluble polymer of the present invention, reacting ratio of the hydrophilic monomer to all other monomers used may be in the range from 90:10 to 10:90 and preferably from 80:20 to 40:60. In case of a copolymer of hydrophobic monomer, the ratio of the monomer to all other monomers used may be from 50:50 to 0:100 and preferably from 40:60 to 20:80, that of a positively charged monomer to all other monomers used may be from 50:50 to 0:100 and preferably from 40:60 to 20:80, that of a negatively charged phosphate-type monomer to all other monomers used may be from 90:10 to 0:100 and preferably from 40:60 to 20:80 and that of a monomer chemically modified with a protein or a peptide to all other monomers used may be from 90:10 to 10:90 and preferably from 50:50 to 20:80.

According to one embodiment of the present invention, the coating composition of the present invention is applied to surface of culture vessels by brushing, spraying, soaking or the like technique, then the solvent is removed by evaporation to form a uniform thin layer of a water-insoluble polymer over the surface. For example, into a dish for cell culture is added the coating composition so as to cover at least the bottom surface of the dish and is allowed to stand in a clean bench to dry up the solvent. Since a lower alcohol that has sterile activity is employed as a solvent, the culture vessels can be used without further sterilization.

According to the present invention, culture vessels may be a multitray, a dish or a bottle made of glass, polystyrene, polycarbonate, polyethylene, polypropylene or other materials. The inner surface of the culture vessels should have been sterilized by a conventional method previous to the coating. In case of plastic vessels, it is desirable to be subjected to the plasma treatment.

In another embodiment, carrier which has been coated with the coating composition of the present invention may be used for culturing an adhesive cell. According to the embodiment, it is possible to increase greatly the area where cells are in contact with the water-insoluble polymer so that a mass culture of cells in a relative small volume of a medium.

The carriers that may be used for this purpose are, for example, fine particles or thin leaves of glass, various synthetic resins and ceramics. The shape and size of these carriers depend on the method and scale of culture and are not particularly specified, but it is noted that in suspension culture, for example, size and specific gravity of the carrier should be selected so that gentle agitation or circulation of the medium can keep the carrier in suspension.

As a fine particle carrier, particles of a water-insoluble polymer that is obtained by suspension polymerization of one of above described monomers and another monomer. The size of the particles of this type of water-insoluble polymer is ordinarily in the range of 100 μm–5 mm and preferably 100 μm–250 μm.

As the adhesive cells to be cultured according to the present invention, general adhesive cells may be with no particular limitation, and examples are epidermal keratinocytes, vascular endothelial cells, mammary epithelial cells, fibroblasts, corneal epithelial cells and other various normal cells and fibrosarcoma cells, glioma cells, tumor blast cells and other various tumor cells as well as established cells.

According to the another aspect of the present invention, there is provided a serum-free culturing method of animal adhesive cells using a culture vessel or a carrier coated with the coating composition of the present invention on at least a part of the surface and culturing the animal adhesive cells in contact with the coating polymer.

Among the above described water-insoluble polymers, such polymers having cell adhesive activity may be employed generally in the method of the present invention. The polymers may be copolymers that containing monomer chemically modified with cell adhesive peptide or positively charged monomer which are described above. Further, in the serum-free culturing method of the present invention, the polymer may be a homopolymer of the above described positively charged monomer.

In case where the polymer is insoluble in a lower alcohol, it may be suspended or dissolved in such an organic solvent as benzene, dioxane and N,N-dimethylformamide, and the solution is applied over the inner surface of a culture vessel and the solvent is removed by evaporation before the vessel is subjected to sterilizing treatment by autoclaving or by γrays irradiation. In this case solvent-resistant or thermoresistant water-insoluble polymers and culture vessels are employed.

For the serum-free culturing method of the present invention, the medium may be selected conveniently from the media with practically same compositions as those used previously for culturing animal adhesive cells except excluding serum. For example, for culturing vascular endothelial cells CHL-MCDB 131 (Chlorella Kogyou Co., Ltd.), MCDB107 (Kyokuto Seiyaku Kogyo Co., Ltd.) and E-BM (Kurashiki Boseki Co., Ltd.) may preferably be employed with adequate growth factors or other ingredients. General conditions of the culture depend on the kind of cells to be cultured but they may be selected conveniently from the culturing conditions hitherto employed.

In the serum-free culturing method of the present invention, adhesive cells to be cultured are transferred stepwise into the serum-free condition. No satisfactory result will be obtained if cell lines that have been cultured in a conventional serum-containing medium or freshly derived cells were directly transplanted into a serum-free medium. In a preferred embodiment, firstly the cells are transplanted into low serum medium such as containing 2% of serum. Secondly, half of the culture medium with so low a serum content is exchanged after every 24 hours with a serum-free medium to decrease the content of serum in the medium gradually. According to the present invention, the cells transferred in this way into a serum-free condition show a growth activity similar to the one observed when cultured in a serum-containing medium, and furthermore they are maintained their functions to be intact. It is noted that vascular endothelial cells that have been difficult to culture previously in serum-free media can now be cultured efficiently in a serum-free condition by the method of the present invention.

According to the present invention, it is also possible to subculture the cells successively in the serum free condition. The cultured cells obtainable in the above described way may be harvested by an ordinary method, for example, by removing from the surface by the use of a mixture of trypsin and EDTA.

A wide range of adhesive cells may be objects of the serum-free culturing method of the present invention, examples are epidermal keratinocyte, vascular endothelial cell, mammary gland epithelial cell, fibroblast, corneal epithelial cell and other normal cells and fibrosarcoma cell, glioma cell and other tumor cells as well as established cells.

EXAMPLES

Below are given examples for more detailed explanation of this invention.

Example 1

Into a 100-ml four-neck reactor equipped with a reflux condenser, mechanical stirrer and thermostat, 10.0 g of 2-hydroxyethyl methacrylate, 5.0 g of n-butyl methacrylate, 5.0 g of diethylaminoethyl methacrylate, 25 ml of isopropanol (solvent) and 20 mg of α,α'-azobisisobutyronitrile (an initiator) were mixed and the mixture was heated at 70° C. for 15 hours under nitrogen stream. The reaction mixture was dropped into 5 liters of distilled water under vigorously stirring to obtain a white, viscous polymer. The polymer was isolated, dissolved in methanol and dropped again into 5 liters of distilled water under vigorously stirring. The same procedure was repeated 3 times, finally the product was collected by filtration with suction and dried in vacuo at 40° C. to obtain a polymer 1 as powder.

Coating composition 1 for culturing adhesive cells was prepared by dissolving the polymer 1 in 70% ethanol to a concentration of 0.001% (10 μg/ml).

Example 2

Polymer 2 was obtained according to the similar way as in Example 1 except that 10.0 g of 2-hydroxyethyl methacrylate and 10.0 g of n-butyl methacrylate were employed as monomers. Polymer 2 was obtained as powder. Coating composition 2 was prepared according to the same way as Example 1.

Example 3

Polymer 3 was obtained according to the similar way as in Example 1 except that 10.0 g of 2-hydroxyethyl methacrylate, 5.0 g of 2-methacryloyloxyethyl-dibutyl phosphate and 5.0 g of diethylaminoethyl methacrylate were employed as monomers. Polymer 3 was obtained in powder. Coating composition 3 was prepared according to the same way as Example 1.

Example 4 i) Into 100 ml of 10% aqueous solution of gelatin (DIFCO), 200 mg of Protease A (Amano Seiyaku Co., Ltd.) was added and incubated at 37° C. for 15 minutes. The reaction mixture was autoclaved at 120° C. for 20 minutes to inactivate the protease. Then the product was dried by evaporation under reduced pressure. Consequently, about 10 g of low molecular weight gelatin was obtained.

ii) One gram of the low molecular weight gelatin of i) was dissolved in 25 ml of 0.1M sodium hydrogencarbonate buffer (pH 11.2). The solution was mixed with 25 ml of N,N'-dimethylformamide and 10.0 g of glycidyl methacrylate, and the mixture was shaken for 15 hours at 30° C. The product was dried by evaporation. Methacrylate in which lower gelatin was incorporated was obtained.

iii) Polymer 4 was obtained according to the similar way as in Example 1 except that 10.0 g of 2-hydroxyethyl methacrylate, 5.0 g of n-butyl methacrylate and 5.0 g of the methacrylate containing lower gelatin of ii) were employed as monomers and N,N'-dimethylformamide was used as a solvent. Polymer 4 was obtained as powder. A part of the polymer 4 was hydrolyzed in 6N hydrochloric acid at 166° C. for 30 minutes and submitted to amino acid analysis to confirm that gelatin was introduced in the polymer. Coating composition 4 was prepared according to the same way as Example 1.

Example 5 i) To 100 g of wool, 500 ml of 35% aqueous hydrogen peroxide was added, and pH of the mixture was adjusted to 8.3 by aqueous ammonia. The mixture was allowed to stand at room temperature for 1 hour to dissolve the wool. Then acetic acid was added to the solution for lower the pH. Alcohol was added to this solution and the mixture was allowed to stand overnight. Then the supernatant was discarded and the precipitate was washed with alcohol and further with acetone followed by drying in air. About 70 g of keratin (the solubilized factor of wool) was obtained as pale yellow powder with no taste.

ii) One gram of the keratin of i) was dissolved in 25 ml of 0.1M sodium hydrogencarbonate buffer (pH 11.2) and mixed with 25 ml of N,N'-dimethylformamide and 10.0 g of glycidyl methacrylate. The mixture was shaken at 30° C. for 15 hours and dried by evaporation. Methacrylate in which the keratin was incorporated was obtained.

iii) Polymer 5 was obtained according to the similar manner as in Example 1 except that 10.0 g of 2-hydroxyethyl methacrylate, 5.0 g of n-butyl methacrylate and 5.0 g of the keratin containing methacrylate of ii) were employed as monomers and N,N'-dimethylformamide was used as a solvent. Polymer 5 was obtained as powder. A part of the polymer 5 was hydrolyzed in 6N hydrochloric acid at 166° C. for 30 minutes, then submitted to amino acid analysis to confirm that keratin was introduced in the polymer. Coating composition 5 was prepared according to the same way as Example 1.

Example 6 i) A scheme for synthesis of the cell adhesive peptide RGDV (Arg-Gly-Asp-Val) by solution method is shown in FIG. 1. Boc-Asp(OcHex) and Val-OBzl were condensed by the WSCI-HOBt method and the Boc group was removed by using trifluoroacetic acid (TFA). Then, Boc-Gly and Asp (OcHex)-Val-OBzl were condensed in the similar way, removed the Boc group and finally Boc-Arg(Tos) and Gly-Asp(OcHex)-Val-OBzl were condensed followed by treatment with anhydrous hydrogen fluoride (HF) treatment to obtain desired RGDV (Arg-Gly-Asp-Val) peptide.

ii) A mixture of 450 mg of the RGDV peptide, 90 mg of methacrylic acid, 190 mg of 1-ethyl-3-(3-dimethylaminopropyl)-carbodiimide hydrochloride, 120 mg of N-hydroxy-succinimide and 5 ml of N,N'-dimethylformamide (solvent) was stirred at 0° C. for 2 hours, follows at room temperature for overnight. To the reaction mixture, 3.6 g of 2-hydroxyethyl methacrylate, 1.0 g of n-butyl methacrylate, 10 ml of N,N'-dimethylformamide and 20 mg of α,α'-azobisisobutyronitrile (initiator) were added and heated at 65° C. for 15 hours under nitrogen stream. Then the reaction mixture was added into 5 liters of distilled water under vigorously stirring to obtain a white, viscous polymer. The polymer was isolated and dissolved in methanol and the solution was again added into 5 liters of distilled water under vigorously stirring. The same procedure was repeated 3 times, then finally the product was filtered with suction and dried in vacuo at 40° C. to obtain polymer 6 as powder. A part of this polymer was hydrolyzed in 6N hydrochloric acid at 166° C. for 30 minutes and submitted to amino acid analysis to confirm that the RGDV (Arg-Gly-Asp-Val) peptide was introduced in the polymer. Coating composition 6 was prepared according to the same way as Example 1.

Comparative Example 1

Collagen type I (Cellmatrix-IC, Nitta Gelatin Co., Ltd.) was dissolved in 70% ethanol to make a 0.001% (10 μg/ml) solution. This solution was used as a coating composition of comparative example 1.

Preparation of culture dishes

One ml each of the coating compositions of example 1–6 and comparative example 1 were added to a commercially available polystyrene dish for suspension cell culture (untreated dish: 35 mm diameter, Sumitomo Bakelite Co., Ltd.: ). The dishes were left in a clean bench overnight to evaporate the solvent completely and the dishes which were coated with the polymers 1–6 and collagen type I were used in cell cultures as follows.

Comparative Example 2

For comparative example 2, untreated dish was used for the following cell culture.

Culture of animal adhesive cells (a) Culture of human glioblastoma cells strain U251-MG Human glioblastoma cells strain U251-MG is a cell line derived from human brain tumor and is an adhesive cell that usually maintained in Dulbecco's Modified of Eagle's Medium (DMEM) containing 10% fetal bovine serum.

Into the each coated or uncoated dishes, 2 ml of the DMEM containing 7% fetal bovine serum was added and $1 \times 10^4$ cells of the human glioblastoma strain U251-MG were inoculated therein. Cell culture was performed in a $CO_2$ incubator adjusted to 37° C. for 7 days. Then, cells were trypsinized and the cell number was counted. The results are shown in Table 1.

(b) Culture of human epidermal keratinocytes (NHEK)

Culture of the normal human epidermal keratinocytes (NHEK) was carried out according to the similar way as in (a) except that a serum-free medium for growth of epidermal keratinocyte (K-GM, Kurashiki Boseki Co., Ltd.) was employed as the medium. The results are shown in Table 1.

(c) Culture of human mammary epithelial cells (HMEC)

Culture of the normal human mammary epithelial cells (HMEC) was carried out according to the similar way as in (a) except that serum-free medium for growth of mammary epithelial cells (MEGM, Kurashiki Boseki Co. Ltd.) was employed as the medium. The results are shown in Table 1.

(d) Culture of human aortic endothelial cells (HAEC)

Culture of the normal human aortic endothelial cells (HAEC) was carried out according to the similar way as in (a) except that a low serum medium for growth of vascular endothelial cells (E-GM, Kurashiki Boseki Co., Ltd.) was employed as culture medium. The results are shown in Table 1.

(e) Culture of human umbilical vein endothelial cells (HUVEC)

Culture of the normal human umbilical vein endothelial cells (HUVEC) was carried out according to the similar way as in (a) except that a low serum medium for growth of vascular endothelial cells (E-GM, Kurashiki Boseki Co., Ltd.) was employed as culture medium. The results are shown in Table 1.

(f) Culture of rabbit corneal epithelial cells (NRCE)

Culture of the normal rabbit corneal epithelial cells (NRCE) was carried out according to the similar way as in (a) except that a serum-free medium for growth of rabbit corneal epithelial cells (RCGM, Kurabo Ind.) was employed as culture medium. The results are shown in Table 1.

TABLE 1

|   | U251-MG | NHEK | HMEC | HAEC | HUVEC | NRCE |
|---|---------|------|------|------|-------|------|
| Example 1 | + | + | + | ++ | ++ | ++ |
| Example 2 | + | + | + | +++ | +++ | +++ |
| Example 3 | − | + | + | + | +++ | + |
| Example 4 | + | ++ | + | +++ | +++ | − |
| Example 5 | ++ | + | + | ++ | ++ | ++ |
| Example 6 | ++ | ++ | ++ | +++ | +++ | − |
| Comparative Example 1 | + | + | + | +++ | +++ | + |
| Comparative Example 2 | − | − | − | − | − | − |

+++ : Cell number was more than 1.5-folds of that found when a plasma-treated 35 φ polystyrene dish was used.
++ : Cell number was 1.2- to 1.5-folds of that found when a plasma-treated 35 φ polystyrene dish was used.
+ : Cell number was 1.0- to 1.2-folds of that found when a plasma-treated 35 φ polystyrene dish was used.
− : Cell number was less than 1.0-fold of that found when a plasma-treated 35 φ polystyrene dish was used.

As obvious from Table 1, by introducing the synthetic RGDV peptide represents the cell adhesive active site of vitronectin or gelatin, which are easier in handling and purification than collagen, into a synthetic polymer, the growth and adhesion of cells was enhanced in comparison when other polymers were used (see Examples 4 and 6). In the cases of NHEK and HMEC, introduction of positively charged or hydrophobic group onto the surface of the culture dishes gave higher growth and adhesion of cells than that when plasma treatment was applied, and introduction of gelatin or RGDV, further increased the growth (see Examples 1 to 3, 4 and 6) In cases of U251-MG and NRCE cells, introduction of keratin increased the growth and adhesion (see Example 5).

Cytotoxicity test

The coating composition 1 obtained in Example 1 was used. One hundred micro liter aliquots of the coating composition 1 were added to each well of a commercially available polystyrene 96-well multiplate (plasma-treated), and allowed the plate to stand in a clean bench overnight to evaporate the solvent completely, then the plates were used in the following cytotoxicity test.

The normal human epidermal keratinocytes (NHEK) in secondary culture were trypsinized, collected and washed and re suspended in the K-GM medium. Then the cells were inoculated at a rate of $2.5 \times 10^3$ of the NHEK cells per well into the above treated wells and incubated for 3 days in a $CO_2$ incubator adjusted to 37° C.

After the 3 days culture, the culture medium was changed with K-GM medium containing various concentration of sodium dodecylsulfate (SDS) while with K-GM medium without SDS as a control. The plate was incubated for 2 more days. The cytotoxcity was estimated by the analysis of uptake of neutral red (3-amino-7-dimethylamino-2-methylphenazine hydrochloride, molecular weight 288.8)

A solution of neutral red in K-GM was added to each well. The plate was incubated for 3 hours. The neutral red is accumulated into the lysosome of viable epidermal keratinocyte, so that the cells whose lysosomal or plasma membrane was injured by the action of the SDS could not take up neutral red. After the incubation, discarding the dye solution and fixation with aqueous solution of formalin-calcium chloride for a short time was done to remove the dye solution that was not taken up and attachment of cells to the plate was enhanced at the same time. The wells were treated with a mixture of acetic acid and ethanol to extract the neutral red that was taken up into the intact cells. Then the absorbance was estimated at 540 nm by using a microplate reader. This absorbance was corresponding to the number of viable cells in each well. The ratio of the absorbance against the control was calculated in percentage (NR).

The absorbance and the NR values are shown together with standard deviation (SD) and coefficient of variance (CV) in Table 2.

Comparative Example 3

Collagen type IV (Cellmatrix-IV, Nitta Gelatin Co., Ltd.) was dissolved in 70% ethanol to prepare a 0.001% (10 µg/ml) solution and 100 µl aliquot of the solution was added to wells of polystyrene 96-well multiplate (plasma-treated). After allowing to stand overnight in a clean bench to evaporate the solvent completely and complete the coating the plate was used in the above cytotoxicity test. The results are shown in Table 2.

Comparative Example 4

A polystyrene 96-well multiplate (plasma-treated) was used with no coating treatment in the above cytotoxicity test. The results are shown in Table 2.

water under vigorously stirring to obtain a white, viscous polymer. The polymer was isolated, dissolved in methanol and dropped again into 5 liters of distilled water under vigorously stirring. The same procedure was repeated 3 times, finally the product was collected by filtration with suction and dried in vacuo at 40° C. to obtain a polymer 7 as crystalline powder.

A part of this polymer was hydrolyzed in 6N hydrochloric acid at 166° C. for 30 minutes and submitted to amino acid analysis to confirm that 17.9 µg of the RGDV peptide was introduced per 1 mg of the polymer. The average molecular weight of the polymer 7 was 50000.

Coating composition 7 for culturing adhesive cells was prepared by dissolving the polymer 7 in 70% ethanol to a concentration of 0.01% (100 µg/ml).

Example 8

Polymer 8 was obtained according to the similar way as in Example 7 except that 0.1 g of the RGDV peptide was used. By amino acid analysis, introduction of 2.1 µg of the RGDV peptide per 1 mg of the polymer 8 was confirmed. The average molecular weight of this polymer was 57000. Coating composition 8 was prepared according to the same way as Example 7.

Example 9

Figure 2:
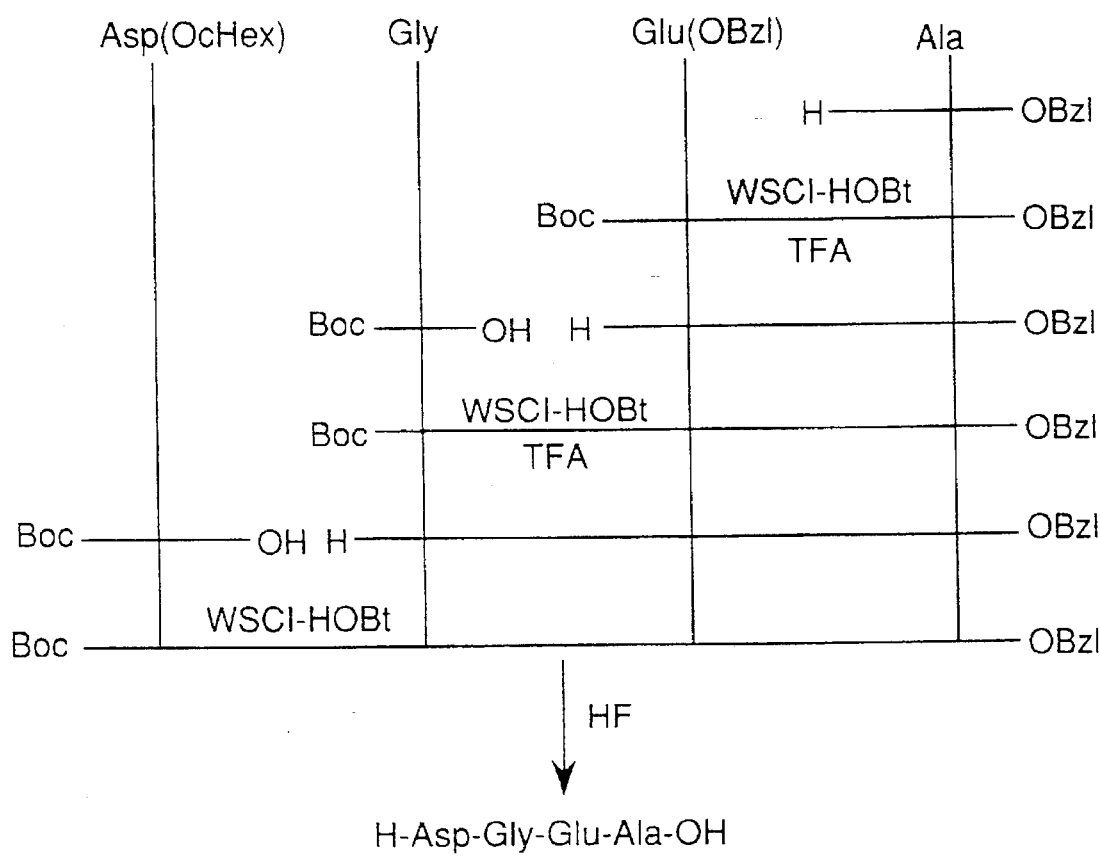
FIG. 2 shows a scheme for synthesis of cell adhesive peptide DGEA.

DGEA peptide (Asp-Gly-Glu-Ala) was synthesized according to the similar way as Example 6. The scheme of this synthesis is shown in FIG. 2.

Polymer 9 was obtained according to the similar way as in Example 7 except that the DGEA peptide was used in place of the RGDV peptide. Polymer 9 was obtained as powder. The result of amino acid analysis showed that 20.5 µg of the DGEA peptide was introduced per 1 mg of the polymer. The average molecular weight of the polymer 9 was 59000. Coating composition 9 was prepared according to the same way as Example 7.

Example 10

Into 5 ml of isopropanol, 0.75 g of 2-hydroxyethyl methacrylate, 0.75 g of n-butyl methacrylate and 0.5 g of

TABLE 2

| | | SDS concentration (µg/ml) | | | | |
|---|---|---|---|---|---|---|
| | | Control | 1.0 | 2.5 | 5.0 | 7.5 |
| Example 1 | Absorbence (540 nm) | 0.555 | 0.416 | 0.261 | 0.163 | 0.096 |
| | NR (%) | — | 75.0 | 47.0 | 29.4 | 17.3 |
| | SD | 0.020 | 0.012 | 0.012 | 0.012 | 0.005 |
| | CV (%) | 3.614 | 2.878 | 4.748 | 7.514 | 4.752 |
| Comparative Example 3 | Absorbance (540 nm) | 0.568 | 0.417 | 0.212 | 0.137 | 0.077 |
| | NR (%) | — | 73.4 | 37.3 | 24.1 | 13.6 |
| | SD | 0.034 | 0.037 | 0.011 | 0.017 | 0.021 |
| | CV (%) | 5.964 | 8.995 | 5.278 | 12.681 | 26.889 |
| Comparative Example 4 | Absorbance (540 nm) | 0.508 | 0.336 | 0.240 | 0.142 | 0.078 |
| | NR (%) | — | 66.1 | 47.2 | 28.0 | 15.4 |
| | SD | 0.057 | 0.024 | 0.023 | 0.023 | 0.010 |
| | CV (%) | 11.273 | 7.009 | 9.580 | 15.987 | 13.090 |

Example 7

The RGDV peptide (0.5 g) that was synthesized previously and 0.5 g of N-methacryloyloxysuccinimide were dissolved in 2.5 ml of N,N'-dimethylformamide (DMF) and the solution was stirred overnight at room temperature. Into the solution, 1.0 g of 2-hydroxyethyl methacrylate, 0.5 g of n-butyl methacrylate, 1 ml of DMF and 20 mg of α,α'-azobisisobutyronitrile (initiator) were added, and the mixture was heated at 65° C. for 15 hours under nitrogen stream. The reaction mixture was dropped into 5 liters of distilled diethylaminoethyl methacrylate were dissolved. Into the solution, 20 mg of an initiator of α,α'-azobisisobutyronitrile was added, and the mixture was heated at 65° C. for 15 hours under nitrogen stream. The reaction mixture was dropped into 5 liters of distilled water under vigorously stirring to obtain a white, viscous polymer. The polymer was isolated, dissolved in methanol and dropped again into 5 liters of distilled water under vigorously stirring. The same procedure was repeated 3 times, finally the product was collected by filtration with suction and dried in vacuo at 40° C. to obtain a polymer 10 as crystalline powder. The average molecular weight of the polymer 10 was 47000. Coating composition 10 was prepared according to the same way as Example 7.

Comparative Example 5

Collagen type I was dissolved in 70% ethanol to prepare a 0.01% (100 μg/ml) solution.
Preparation of culture dishes One ml aliquots of the coating composition of examples 7–10 and comparative example 5 were added to commercially available 35 mm diameter polystyrene dishes for cell culture (Petri dish for cell culture (plasma-treated), Sumitomo Bakelite Co., Ltd.). The dishes were allowed to stand overnight in a clean bench to evaporate the solvent completely and complete the coating, then used for following cell culture.

The dishes coated with the polymers 7–10 showed little release of the cells and maintained normal cell morphology after culturing for 5 days with the serum-free medium. On the other hand, in the comparative examples, dish which coated with collagen or untreated showed extensive release of cells and gave deformed cells.

After culturing for 5 days in the serum-free DMEM, the cells were harvested by trypsinization. The collected cells were inoculated into newly prepared by coating of above 7–10 polymers and 2 ml aliquots of the serum-free DMEM added dishes in a rate of $2 \times 10^4$ cells per dish. The dishes were further cultured in the $CO_2$ incubator at 37° C. for 24 hours then cell morphology was observed with a phase-contrast microscope after 24 hours. The results are shown in Table 3.

TABLE 3

Cell: Human glioblastoma cell strain U251-MG
Medium: The Dulbecco's Modification of Eagle's Medium

| Example/ Comparative Example | Coating polymer | 6 days in 2% serum-containing medium | 5 days after exchange with serum-free medium | After 24 hour subculture in serum-free medium |
|---|---|---|---|---|
| | | Number of viable cells ($\times 10^5$/dish) | | |
| Example 7 | 7 | 2.85 | 2.15 | Cells attached and spread on the dish |
| Example 8 | 8 | 2.58 | 1.82 | Cells attached and spread on the dish |
| Example 9 | 9 | 2.58 | 1.88 | Cells attached and spread on the dish |
| Example 10 | 10 | 3.38 | 2.16 | Cells attached and spread on the dish |
| Comparative Example 5 | Collagen I | 2.98 | 1.15 | |
| Comparative Example 6 | None | 2.78 | 0.40 | |

Comparative Example 6

As comparative example 6, uncoated dish was used for the following cell culture.
Serum-free culture of animal adhesive cells
(g) Culture of human glioblastoma cells strain U251-MG The human glioblastoma cells strain U251-MG that were cultured in the DMEM containing 10% fetal bovine serum were suspended in DMEM containing 2% fetal bovine serum to be a concentration of $2 \times 10^4$ cells/ml, and dispensed in 2 ml aliquot into the above coated dishes and incubated in a $CO_2$ incubator adjusted to 37° C.

The cells were cultured for 6–8 days until they reached to be confluent. After the cells had reached to be confluent, 1 ml of the culture medium in each dish was taken away and 1 ml of serum-free DMEM was added to each dish to make the serum concentration of the culture medium to be 1%. The same procedure was repeated every 24 hours to decrease the serum concentration of the culture medium successively to 0.5%, 0.25% and 0.125%. After culturing in the DMEM containing 0.125% serum for 24 hours, all the medium in the dish was exchanged with 2 ml of serum-free DMEM medium.

After culturing for 5 days in the serum-free DMEM, the cells were harvested by trypsinization and the number of viable cells was counted.

As a standard culture, the same number of the inoculum cells were cultured in the above coated dishes with DMEM containing 2% of serum for 6 days and the number of viable cells was counted.

(h) Culture of human neuroblastoma cells strain SK-N-MC

Like U251-MG, human neuroblastoma cells strain SK-N-MC is a cell line derived from human brain tumor and is an adhesive cell line which is usually maintained in the DMEM containing 10% fetal bovine serum.

The SK-N-MC cells which were cultured in the DMEM containing 10% fetal bovine serum were subjected to serum-free culture according to the manner similar as in (g). Number of viable cells was counted 5 days after the start of serum-free culture, and 6 days after culturing in the DMEM containing 2% serum after inoculation.

The dishes coated with the polymers 7–10 showed little release of the cells and maintained normal cell morphology after culturing for 5 days with the serum-free medium. On the other hand, in the comparative examples, dish which coated with collagen or uncoated showed extensive release of cells and gave deformed cells.

After culturing for 5 days in the serum-free DMEM, cells were harvested by trypsinization. Dishes were newly prepared by coating with the polymers 7–10 and 2 ml aliquots of the serum-free DMEM were added therein. Into the dishes, $2 \times 10^6$ of each cells that were obtained from the above cultures were inoculated. The dishes were cultured in the $CO_2$ incubator at 37° C. for 24 hours. The morphology of cells was observed under a phase-contrast microscope. The results are shown in Table 4.

TABLE 4

Cell: Human glioblastoma cell strain SK-N-MC
Medium: The Dulbecco's Modification of Eagle's Medium

| Example/<br>Comparative Example | Coating polymer | Number of viable cells (× 10⁵/dish) | | After 24 hour subculture in serum-free medium |
|---|---|---|---|---|
| | | 6 days in 2% serum-containing medium | 5 days after exchange with serum-free medium | |
| Example 7 | 7 | 3.50 | 2.85 | Cells attached and spread on the dish |
| Example 8 | 8 | 2.65 | 1.87 | Cells attached and spread on the dish |
| Example 9 | 9 | 2.95 | 2.37 | Cells attached and spread on the dish |
| Example 10 | 10 | 3.53 | 2.03 | Cells attached and spread on the dish |
| Comparative Example 5 | Collagen I | 2.78 | 1.20 | |
| Comparative Example 6 | None | 2.48 | 0.15 | |

(i) Culture of human umbilical vein endothelial cells (HUVEC)

The normal human umbilical vein endothelial cells obtained from the culture kit (Endocell kit, Kurashiki Boseki Co., Ltd.) which were secondarily cultured in a low serum medium for growth of vascular endothelial cells (E-GM UV, Kurashiki Boseki Co., Ltd.) were used. E-GM UV was a medium made by adding to a basal medium for vascular endothelial cells (E-BM) an epithelial growth factor (EGF, 10 µg/ml), hydrocortisone (1 µg/ml), antibacterial agents (Gentamicin, 50 µg/ml; amphotericin, 0.25 µg/ml) and bovine brain extract (BBE, 0.4% v/v).

HUVEC were cultured according to the similar way as in (g) above. Initially the low serum medium for growth of vascular endothelial cells (E-GM UV) containing 2% fetal bovine serum was used, and after the cells have reached to confluence, the amount of serum was decreased stepwise as in (g) and then exchanged with a completely serum free medium. Number of viable cells was counted 2 days after the start of serum-free culture, and 6 days after culturing in the E-GM UV containing 2% serum after inoculation. The results are shown in Table 5.

TABLE 5

Cell: Human umbilical vein endothelial cell (HUVEC)
Medium: Low serum medium for propagation of
vascular endothelial cell (E-GM UV) (without serum)

| Example/<br>Comparative Example | Coating polymer | Number of viable cells (× 10⁵/dish) | |
|---|---|---|---|
| | | 6 days in 2% serum-containing medium | 2 days after exchange with serum-free medium |
| Example 7 | 7 | 3.10 | 2.63 |
| Example 8 | 8 | 2.73 | 2.45 |
| Example 9 | 9 | 2.92 | 2.73 |
| Example 10 | 10 | 3.02 | 2.65 |
| Comparative Example 5 | Collagen I | 3.78 | 2.05 |
| Comparative Example 6 | None | 2.15 | 0.25 |

The dishes coated with the polymers 7–10 showed little release of the cells and maintained normal cell morphology under the serum-free condition. On the other hand, in the comparative examples, dish which coated with collagen or uncoated showed extensive release of cells and gave deformed cells.

(j) Production of endothelin by cultured human umbilical vein endothelial cells (HUVEC)

The HUVEC cultured in the dishes coated with the polymers 7–10, which maintained normal cell morphology, and in the untreated dish were employed 2 days after the exchange with the serum-free E-GM UV medium by the method described in (i) above. All of the culture medium was exchanged with fresh serum-free E-GM UV and the dishes were cultured more 24 hours. Then, the medium was isolated and the amount of endothelin contained in the medium was estimated. As a control, the amount of endothelin produced by the HUVEC that was cultured until reaching to confluence in the medium E-GM UV containing 2% fetal bovine serum in each dish was estimated. Estimation of endothelin was done by using an endothelin-1 estimation kit (Kokusai Shiyaku Co., Ltd). The results are shown in Table 6.

TABLE 6

| Example/<br>Comparative Example | Coating polymer | Yield of endothelin (pg/dish) | |
|---|---|---|---|
| | | At cell confluence in 2% serum-containing medium | 2 days after exchange with serum-free medium |
| Example 7 | 7 | 581 | 441 |
| Example 8 | 8 | 304 | 182 |
| Example 9 | 9 | 607 | 450 |
| Example 10 | 10 | 368 | 277 |
| Comparative Example 6 | None | 484 | 12 |

It was found that in the serum-free culture the potency of endothelin production was retained showing that the function of vascular endothelial cells were maintained to be normal.

By using a coating composition for culturing adhesive cells of the present invention, adhesion and growth of the adhesive cells can be enhanced effectively without requirement of a special apparatus for culture or additional sterilizing process.

In addition, by the method of this invention adhesion and growth of a wide range of animal adhesive cells can be enhanced effectively and the serum-free culture of the cells is made possible. The cells that are obtained by the serum-free culture do not lose their intrinsic functions, for example, the vascular endothelial cells cultured by this technique retain the potency to produce endothelin. It must be noted that the cultured cells that have once been transferred to a serum-free medium can be subcultured thereafter under serum-free conditions.

What is claimed:

1. A serum-free culturing method of animal adhesive cells comprising: 1) coating the surface of a culture vessel or a carrier with a water-insoluble polymer dissolved in a lower alcohol or an aqueous lower alcohol; wherein the said lower alcohol is selected from methanol, ethanol, propanol and butanol; wherein said polymer contains as monomer ingredients at least one monomer chemically bound to a peptide having a cell adhesive activity, said monomer being selected from the group consisting of (metha)acrylic acid, glycidyl (metha)acrylate and N-(metha)acryloyloxy succinimide, wherein the concentration of the water-insoluble polymer in the lower alcohol or aqueous lower alcohol is from about 0.001 to about 0.1% (w/v); wherein the amount of the peptide having cell adhesive activity is greater than about 2 µg/mg of the polymer; and wherein the polymer has a formulation ratio of hydrophilic monomers to all other monomers in the range from 90:10 to 10:90; and 2) culturing the animal adhesive cells in the vessel or carrier using a medium which contains no serum while in contact with the polymer.

2. A serum-free culturing method of animal adhesive cells of claim 1, wherein said hydrophilic monomers comprise at least one hydrophilic monomer selected from the group consisting of hydroxyethyl (metha)acrylate, pentaerythritol (metha)acrylate, oligoethyleneglycol (metha)acrylate, oligopropyleneglycol (metha)acrylate and a mixture thereof.

3. A serum-free culturing method of animal adhesive cells of claim 1, in which the water-insoluble polymer additionally contains as one of the monomer ingredients a hydrophobic monomer selected from the group consisting of methyl (metha) acrylate, ethyl (metha) acrylate, n-propyl (metha) acrylate, isopropyl (metha) acrylate, n-butyl (metha) acrylate, isobutyl (metha)acrylate, t-butyl (metha) acrylate, and a mixture thereof.

4. A serum-free culturing method of animal adhesive cells of claim 1, in which the carrier is selected from the group consisting of fine particles, film, net, and woven cloth.

5. A serum-free culturing method of animal adhesive cells of claim 1, wherein a peptide having a cell adhesive activity is a peptide selected from the group consisting of RGDV (Arg-Gly-Asp-Val), RGDS (Arg-Gly-Asp-Ser), RGDN (Arg-Gly-Asp-Asn), DGEA (Asp-Gly-Glu-Ala) and YIGSR (Tyr-Ile-Gly-Ser-Arg) peptides.

6. A serum-free culturing method of claim 1, in which the peptide has 5 or less than 5 amino acid moieties.

7. A serum-free culturing method of claim 1, in which the peptide has 4 or 5 amino acid moieties.

8. A serum-free culturing method of claim 1, in which the peptide contains as amino acid moieties amino acids selected from the group consisting of Ala, Arg, Asn, Asp, Ile, Glu, Gly, Ser, Try, Val and mixture thereof.

9. A serum-free culturing method of claim 1, in which the polymer has a formulation ratio of the monomers chemically bound to a peptide having a cell adhesive activity to all other monomers from 90:10 to 10:90.

10. A serum-free culturing method of claim 1, in which the polymer has a formulation ratio of the monomers chemically bound to a peptide having a cell adhesive activity to all other monomers from 50:50 to 20:80.

11. A serum-free culturing method of claim 2, in which the ratio of hydrophilic monomers to all other monomers is from 80:20 to 40:60.

12. A serum-free culturing method of claim 3, in which the ratio of hydrophobic monomers to all other monomers is from 50:50 to 0:100.

13. A serum-free culturing method of claim 3, in which the ratio of hydrophobic monomers to all other monomers is from 40:60 to 20:80.

14. The method as claimed in claim 1, wherein the concentration is from about 0.001 to about 0.01% (w/v).

15. The method as claimed in claim 1, wherein the amount of the peptide having cell adhesive activity is from about 2 to about 18 µg/mg of the polymer.

16. The method as claimed in claim 1, wherein the animal adhesive cells are selected from the group consisting of human glioblastoma cells, human epidermal keratinocytes, human mammary gland epithelial cells, human aorta endothelial cells, human umbilical vein endothelial cells, rabbit corneal epithelial cells, and human neuroblastoma cells.

17. A serum-free culturing method of claim 1, in which the aqueous lower alcohol contains from about 50% to about 90% of lower alcohol.

18. A serum-free culturing method of claim 1, wherein said peptide comprises RGDV and said monomer ingredients comprise N-methacryloyloxysuccinimide, 2-hydroxyethyl methacrylate, and n-butyl methacrylate.

19. A serum-free culturing method of claim 1, wherein said peptide comprises DGEA and said monomer ingredients comprise N-methacryloyloxysuccinimide, 2-hydroxyethyl methacrylate, and n-butyl methacrylate.

20. A serum-free culturing method of claim 1, wherein said method includes a first step of polymerizing said at least one monomer.

* * * * *